United States Patent [19]

Peters

[11] 4,271,704
[45] Jun. 9, 1981

[54] FLUID SAMPLING DEVICE AND METHOD OF SAMPLING FLUID
[75] Inventor: Beldon A. Peters, Houston, Tex.
[73] Assignee: Exxon Production Research Company, Houston, Tex.
[21] Appl. No.: 82,341
[22] Filed: Oct. 5, 1979
[51] Int. Cl.³ ............................................. G01N 1/12
[52] U.S. Cl. ................................ 73/864.63; 116/264; 166/264
[58] Field of Search .................... 73/425.4 R; 116/264

[56] References Cited

U.S. PATENT DOCUMENTS

| | | | |
|---|---|---|---|
| 1,591,511 | 7/1926 | Cavins | 166/163 |
| 3,055,764 | 9/1962 | Pryor et al. | 166/264 |
| 3,277,723 | 11/1966 | Bodman et al. | 73/425.4 R |
| 3,377,868 | 4/1968 | Dowling et al. | 73/425.4 R |
| 3,892,130 | 7/1975 | Wignet et al. | 73/425.4 R |
| 4,004,463 | 1/1977 | Puthoff et al. | 73/425.4 R |

Primary Examiner—Daniel M. Yasich
Attorney, Agent, or Firm—Robert B. Martin

[57] ABSTRACT

An apparatus and method for sampling fluids is disclosed where the apparatus includes a body having a chamber therein, a control valve disposed in a control passageway in the body and a sample valve disposed in the sampling passageway in the body. The sample valve includes a freely movable valve member having a specific gravity less than the steps of pressurizing the chamber to force the valve member into sealing engagement with the sampling passageway and lowering the device into the fluid to be sampled to a predetermined depth were in the hydrostatic pressure on the valve enables the valve to move into the chamber permitting sampling fluid to fill the chamber. The sample valve floats on the fluid and seals the chamber when it is filled.

4 Claims, 2 Drawing Figures

FLUID SAMPLING DEVICE AND METHOD OF SAMPLING FLUID

BACKGROUND OF THE INVENTION

1. Field of the Invention

The present invention pertains to methods and apparatus for sampling fluids and, more particularly, to such methods and apparatus useful for sampling fluid discharged from the bottom of a downcomer pipe extending into a body of water from an offshore drilling platform.

2. Description of the Prior Art

Drill cuttings from offshore drilling operations are normally discarded to the sea floor from a single offshore platform during the drilling of a large number of wells. It is desirable that these drill cuttings be free from any petroleum based compounds. To remove oil from the drill cuttings before they are discarded onto the sea floor, it is conventional to pass the drill cuttings through a long, vertical pipe extending from the surface of the sea to a few hundred feet below the surface. This pipe is normally referred to as a downcomer pipe. As the drill cuttings are passed down through the downcomer pipe, the oil is washed from the drill cutting and floats toward the surface of the water in the downcomer pipe. The oil remains at the surface of the water and is occasionally skimmed off and pumped out. To ensure that the sea water is not being contaminated with oil, it is desirable to periodically sample the sea water near the bottom of the downcomer pipe. In the past, pumps have been placed in the downcomer pipe near the sampling location to deliver samples of the sea water to the surface. Unfortunately, the drill cuttings in the samples ruin the pumps and renders their operating lives extremely short and unreliable. Attempts to run conventional fluid samplers down the downcomer pipe have had the disadvantage that the oil and sludge near the surface of the water in the downcomer pipe completely coat the sample chamber and mix with the sample resulting in non-representative samples.

There are many other situations where it is desired to sample a fluid at a predetermined depth; however, prior art fluid sampling devices and methods have had the disadvantages of being relatively complex and of not obtaining a true representative sample due to contaminants in the fluid above the predetermined depth. U.S. Pat. Nos. 3,815,422 to Niskin, 3,892,130 to Winget et al, 4,037,477 to Niskin, and 4,050,315 to Markfelt and British Patent Nos. 566,752 and 1,107,180 are representative of prior art fluid sampling devices operable to obtain fluid samples at predetermined depths.

SUMMARY OF THE INVENTION

Accordingly, the present invention overcomes the above-mentioned disadvantages of the prior art by providing both a method of sampling fluids and a fluid sampling device which are relatively simple and are capable of obtaining a representative fluid sample at predetermined depths.

The fluid sampling device of the present invention generally includes a body having a chamber therein, a sampling passage extending througn an upper portion of the body and a control passage extending through the body. A control valve is disposed in the control passage for admitting a pressurizing fluid to the chamber. A sample valve is disposed in the sampling passage and including an annular valve seat and a valve member. The valve member has a spherical configuration is freely moveable within said chamber. The valve member has a specific gravity less than the specific gravity of the fluid to be sampled and the valve member can be maintained in engagement with the valve seat by injecting pressurizing fluid into the chamber. The valve member can be moved away from the valve seat when the pressure of the fluid to be sampled on the valve member overcomes the pressure of the pressurizing fluid in the chamber. Thereby enabling the sampling fluid to enter into the chamber. The valve member floats on the fluid to be sampled and as the chamber is filled with the fluid the valve member engages the valve seat to seal the chamber.

The method of the present invention involves sampling fluids at a predetermined depth with a fluid sampling device of the present invention. The method generally comprises the steps of first pressurizing the chamber of the device to force the valve member into sealing engagement with the sampling passage. The pressure within the chamber is substantially the same as the pressure of the fluid to be sampled at the predetermined depth. Second, lowering the fluid sampling device to the predetermined depth in the fluid to be sampled where the fluid pressure on the valve member overcomes the pressure in the chamber on the valve member to move the valve member away from the sampling passage and permit the chamber to be filled with the fluid to be sampled. As the sampling fluid enters the chamber it forces the buoyant valve member into sealing engagement with the sampling passage when the chamber is filled. Third, raising the fluid sampling device from the fluid to be sampled. Fourth, discharging the fluid from the chamber. The fluid may be discharged from the device by inverting the body of the fluid sampling device to cause the valve member to float away from the sampling passage and permit the fluid in the chamber to flow from the chamber through the sampling passage.

One advantage of the present invention is the ease of operation in opening the sampling valve at the predetermined depth. The depth at which the sample valve in the fluid sampling device opens is controlled by the degree of pressurization of the chamber prior to lowering of the fluid sampling device and does not require intricate operating mechanisms therefor or the measurement of depth to which the fluid sampling device has been lowered. Another advantage of the fluid sampling device is that it has a simple structure and is inexpensive to manufacture. Thus, the method and apparatus of the present invention provide a relatively simple procedure for obtaining contaminant-free-fluid samples. Other advantages of the present invention will become apparent from the following description of the preferred embodiment taken in conjunction with the accompanying drawings.

DESCRIPTION OF THE PREFERRED EMBODIMENT

Figure 1:
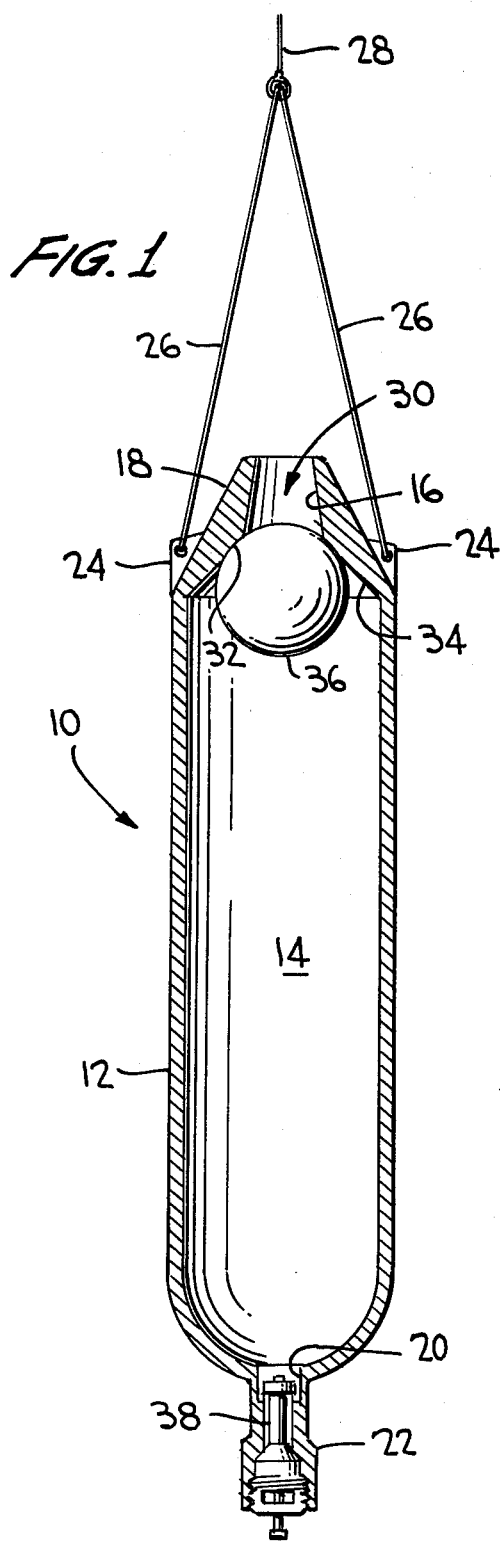
FIG. 1 is a cross sectional view of a fluid sampling device according to the present invention.

A preferred embodiment of a fluid sampling device 10, according to the present invention, is shown in FIG. 1 and generally includes a hollow body 12 defining an interior chamber 14 and having a conical sampling passage 16 extending through a conical nose 18 at an upper portion of the body and a control passage 20 extending through a nipple 22 axially aligned with the sampling passage 16 in a lower portion of the body. The body 12 carries ears 24 for receiving bridal wires 26 connected with a running line 28.

A sample valve 30 is disposed in sampling passage 16 and includes an annular valve seat 32 formed at the junction of sampling passage 16 with an internal conical portion 34 in nose 18 and a spherical or ball valve member 36 freely movable within the chamber 14. The valve seat 32 is located in the sampling passage 16 at a position spaced from the end of the sampling passage to define an open cavity above the sample valve 30. The ball valve member 36 is made of a suitable material to have a specific gravity less than the specific gravity of the fluid to be sampled such that, when the chamber 14 is filled with a fluid to be sampled, the ball valve member 36 will float on the fluid to engage valve seat 32.

A control valve 38 is positioned in passage 20 and is conventional in structure to permit the controlled passage of a pressurizing fluid, such as air, therethrough. For example, the control valve 38 could be of the type used in bicycle and automobile tires, it being of primary importance only that the control valve 38 maintain pressure in chamber 14 when closed.

The operation of the fluid sampling device 10 will be described with reference to FIG. 2 in accordance with a method of sampling water discharged from a downcomer pipe 40 extending from an offshore drilling platform 42 into a body of water according to the present invention; however, the fluid sampling device 10 can be used in any suitable fluid sampling application, such as in wells. Drill cuttings removed during drilling in the sea floor are directed to the downcomer pipe 40 via a delivery system 44 and pass through an oil skimmer 46 at the top of the downcomer pipe before being discharged from the bottom of the downcomer pipe for deposit on the sea floor.

In accordance with the method of the present invention for sampling fluids using a fluid sampling device 10 of the present invention, the body 12 is inverted to position the nose 18 at the bottom such that the ball valve member 36 engages the valve seat 32, and the chamber 14 is filled with air via control valve 38 to a pressure substantially the same as the hydrostatic pressure at the depth where the sample is to be taken. For example, if it is desired to sample water seventy feet below the surface, the pressure in the chamber 14 will be $70 \times (0.444) = 31$ psig. The pressure in chamber 14 forces ball valve member 36 against valve seat 32 such that the sample valve 30 remains closed when the body 12 is returned to the upright position shown in FIG. 1. The fluid sampling device and the bridal wires are now sprayed with a detergent to prevent oil and sludge from clinging to the exterior of the fluid sampling device as the device is lowered down the downcomer pipe to the sampling zone adjacent the bottom of the downcomer pipe and to facilitate the rapid removal of any oil or sludge on the fluid sampling device by washing once the fluid sampling device is withdrawn from the downcomer pipe thereby avoiding contamination of the water sample. The cavity at the top of sampling passage 16, which preferably has a volume of less than 1% of the volume of chamber 14, is now filled with water to prevent oil and sludge from collecting therein as the fluid sampling device is lowered through the oil at the water surface.

Figure 2:
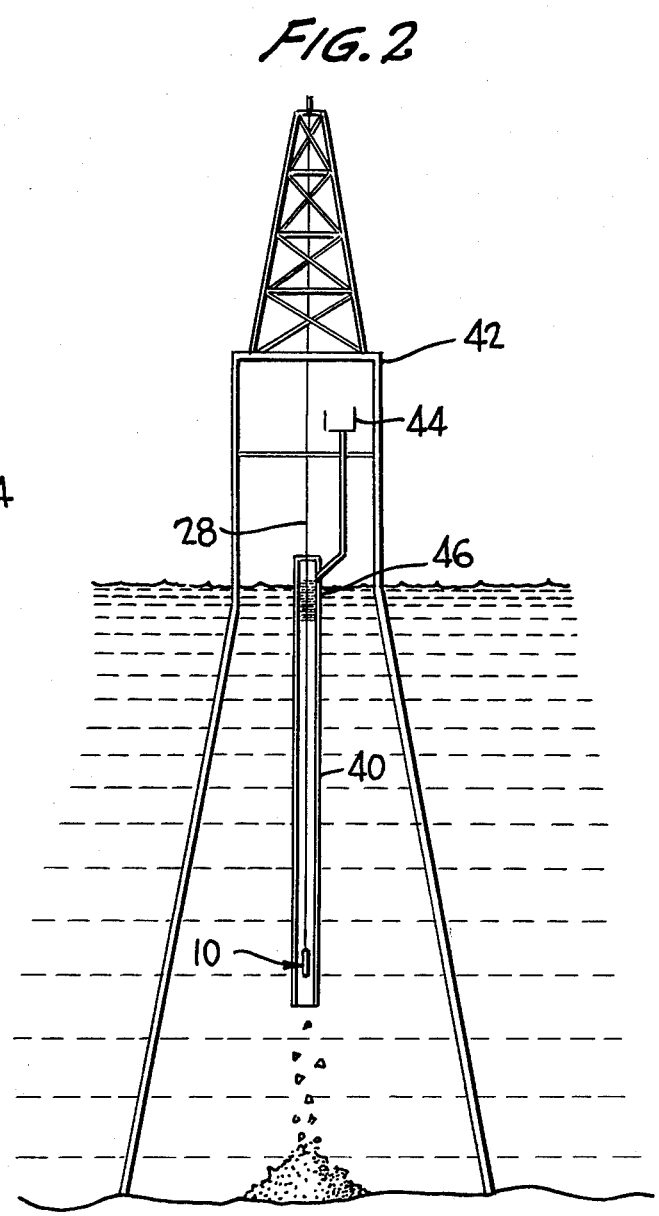
FIG. 2 is a diagrammatic illustration of a drilling platform utilizing a fluid sampling device according to the present invention for sampling water near the bottom of a downcomer pipe.

The fluid sampling device is now lowered on the running line 28 through the downcomer pipe 40 to the sampling zone adjacent the bottom of the downcomer pipe, as shown in FIG. 2; and, at the sampling zone, the hydrostatic pressure of the water on the ball valve member 36 will overcome the internal pressure in the chamber 14 on the ball valve member to cause the ball valve member 36 to move from valve seat 32 and drop into the air-filled chamber. As the ball valve member drops, air from the chamber escapes through sampling passage 16 and is replaced by sea water at the sampling depth. As the water fills the chamber, the ball valve member 36 will float on the water and rise to a position to engage valve seat 32 and seal the chamber 14. The cavity at the top of passage 16 will also be filled with water at the sampling depth such that, when the fluid sampling device 10 is pulled up through the downcomer pipe 40, the water in the cavity prevents oil from the water surface from accumulating therein.

Once the fluid sampling device 10 is retrieved above the water surface, air may be supplied via the control valve 38 to assure that the ball valve member 36 is securely seated on the valve seat 32; and, with the sample valve 30 securely closed, the exterior of the fluid sampling device including the cavity at the top of the sampling passage 16 is washed thoroughly to remove any traces of oil. The washed fluid sampling device is then inverted and placed on a sample receiver, and air pressure may be relieved through control valve 38 such that the ball valve member 36 will float upward in the sample away from the valve seat 32 to open the sample valve 30 and permit the water sample to flow through sampling passage 16 into the sample receiver.

While an embodiment and application of this invention has been shown and described, it will be apparent to those skilled in the art that many more modifications are possible without departing from the inventive concepts herein described. The invention, therefore, is not to be restricted except as is necessary by the prior art and by the spirit of the appended claims.

What I claim is:

1. A method of sampling fluid at a predetermined depth with a fluid sampling device including a body having a chamber therein and a sampling passage and control passage communicating with said chamber and a freely movable valve member disposed in said chamber and having a specific gravity less than the specific gravity of the fluid to be sampled and a control valve disposed in said control passage, said method comprising the steps of:
   (a) pressurizing the chamber with a gas through said control passage to force said valve member into sealing engagement with said sampling passage, the pressure within said chamber being substantially the same as the pressure of the fluid to be sampled at the predetermined depth;
   (b) lowering the fluid sampling device to the predetermined depth in the fluid to be sampled where the fluid pressure on said valve member enables said valve member to move away from said sampling passage and permit the chamber to be filled with said fluid to be sampled, said fluid forcing said valve member floating on said fluid into sealing engagement with the sampling passage when said chamber is filled;

(c) raising the fluid sampling device from the fluid to be sampled; and (d) discharging the fluid from said chamber.

2. The method as recited in claim 1 wherein an open cavity is disposed above said valve member in said sampling passage and further comprising, prior to said lowering step, the step of filling the cavity with fluid to prevent contamination of the sampled fluid by fluid above the predetermined depth.

3. The method as recited in claim 1 and further comprising, prior to said lowering and filling steps, the step of spraying the exterior of said fluid sampling device with a detergent to prevent contaminants from clinging to the fluid sampling device.

4. A method of sampling fluid discharged from the bottom of a down-comer pipe extending into a body of water from an offshore drilling platform comprising the steps of:

(a) pressurizing a chamber in the body of a fluid sampling device with a gas to force a freely movable valve member having a specific gravity less than the specific gravity of the water in said chamber to seat in a sampling passage communicating with said chamber and extending above the seated valve member to form an open cavity, the pressure within said chamber being at least the same as the hydrostatic pressure of the water at the bottom of the downcomer pipe;

(b) filling said cavity with water;

(c) lowering said fluid sampling device down the downcomer pipe to a location where the hydrostatic pressure on said valve member causes said valve member to move away from said sampling passage and permit said chamber to fill with water, thereafter the entering water forcing said valve member floating on the water to seat in said sampling passage when said chamber is filled;

(d) raising the fluid sampling device through the downcomer pipe;

(e) washing the exterior of the fluid sampling device; and (f) discharging the water from the chamber.

* * * * *